US006713281B2

(12) United States Patent
Short

(10) Patent No.: US 6,713,281 B2
(45) Date of Patent: Mar. 30, 2004

(54) DIRECTED EVOLUTION OF THERMOPHILIC ENZYMES

(75) Inventor: Jay M. Short, Encinitas, CA (US)

(73) Assignee: Diversa Corporation, San Diego, CA (US)

( * ) Notice: Subject to any disclaimer, the term of this patent is extended or adjusted under 35 U.S.C. 154(b) by 0 days.

(21) Appl. No.: 10/039,293

(22) Filed: Dec. 31, 2001

(65) Prior Publication Data

US 2003/0073165 A1 Apr. 17, 2003

Related U.S. Application Data

(63) Continuation of application No. 09/185,373, filed on Nov. 3, 1998, now Pat. No. 6,335,179, which is a continuation of application No. 08/760,489, filed on Dec. 5, 1996, now Pat. No. 5,830,696.
(60) Provisional application No. 60/008,311, filed on Dec. 7, 1995.

(51) Int. Cl.[7] ............................ C12P 21/06; C07K 17/00
(52) U.S. Cl. ....................................... 435/69.1; 530/350
(58) Field of Search ............................ 435/69.1; 530/350

(56) References Cited

U.S. PATENT DOCUMENTS

| 4,683,202 A | 7/1987 | Mullis |
| 4,800,159 A | 1/1989 | Mullis et al. |
| 4,959,312 A | 9/1990 | Sirotkin |
| 4,965,188 A | 10/1990 | Mullis et al. |
| 5,096,815 A | 3/1992 | Ladner et al. |

(List continued on next page.)

FOREIGN PATENT DOCUMENTS

| EP | 0 285 123 | 10/1988 |
| EP | 0 316 018 A2 | 5/1989 |
| WO | WO 90/02809 | 3/1990 |
| WO | WO 91/12341 | 8/1991 |
| WO | WO 91/16427 | 10/1991 |

(List continued on next page.)

OTHER PUBLICATIONS

Arkin and Youvan, "Optimizing nucleotide mixtures to encode specific subsets of amino acids for semi–radom mutagenesis," *Bio–technology (NY)* 10(3):297–300 (Mar. 1992).

Burks et al., "In–vitro scanning saturation mutagenesis of an antibody binding pocket," *Proc Natl Acad Sci USA* 94(2): 412–417 (Jan. 21, 1997).

Chen and Struhl, "Saturation mutagenesis of a yeast hls3"TATA element": genetic evidence for a specific TAT-A–binding protein," *Proc Natl Acad Sci USA* 85(8):2691–2695 (Apr. 1988).

Chiang et al., "Mutagenic oligonucleotide–directed PCR amplification (Mod–PCR): an efficient method for generation random base substitution in a DNS sequence element," *PCR Methods Appl* 2(3): 210–217 (Feb. 1993).

Christian et al, "Simplified methods for construction, assessment and rapid screening of peptide libraries in bacteriophage," *J Mol Biol* 227(3):711–718 (Oct. 5, 1992).

Cunniff and Mrogan, "Analysis of heat shock element recognition by saturation mutagenesis of the human *HSP70.1* gene promoter," J. Biol Chem 268(11):8317–8324 (Apr. 15, 1993).

(List continued on next page.)

Primary Examiner—Hankyel T. Park
(74) Attorney, Agent, or Firm—Jane M. Love; Hale and Dorr LLP

(57) ABSTRACT

Thermostable enzymes are subjected to mutagenesis to produce a thermophilic enzyme which is stable at thermophilic temperature and which has increased activities at least two-fold higher than the activity of the wild-type thermostable enzyme at lower temperatures, which are temperatures of 50° C. or lower.

92 Claims, 3 Drawing Sheets

U.S. PATENT DOCUMENTS

| | | |
|---|---|---|
| 5,176,995 A | 1/1993 | Sninsky et al. |
| 5,187,083 A | 2/1993 | Mullis |
| 5,198,346 A | 3/1993 | Ladner et al. |
| 5,223,408 A | 6/1993 | Goeddel et al. |
| 5,223,409 A | 6/1993 | Ladner et al. |
| 5,234,824 A | 8/1993 | Mullis |
| 5,333,675 A | 8/1994 | Mullis et al. |
| 5,352,778 A | 10/1994 | Comb et al. |
| 5,354,656 A | 10/1994 | Sorge et al. |
| 5,389,537 A | 2/1995 | Raines et al. |
| 5,500,363 A | 3/1996 | Comb et al. |
| 5,512,463 A | 4/1996 | Stemmer |
| 5,605,793 A | 2/1997 | Stemmer |
| 5,645,988 A | 7/1997 | Vande Woude et al. |
| 5,658,727 A | 8/1997 | Barbas et al. |
| 5,723,323 A | 3/1998 | Kauffman et al. |
| 5,759,817 A | 6/1998 | Barbas |
| 5,763,192 A | 6/1998 | Kauffman et al. |
| 5,789,166 A | 8/1998 | Bauer et al. |
| 5,798,208 A | 8/1998 | Crea |
| 5,811,238 A | 9/1998 | Stemmer et al. |
| 5,814,476 A | 9/1998 | Kauffman et al. |
| 5,817,483 A | 10/1998 | Kauffman et al. |
| 5,824,469 A | 10/1998 | Horwitz et al. |
| 5,824,485 A | 10/1998 | Thompson et al. |
| 5,824,514 A | 10/1998 | Kauffman et al. |
| 5,830,696 A * | 11/1998 | Short .................... 435/69.1 |
| 5,830,721 A | 11/1998 | Stemmer et al. |
| 5,837,458 A | 11/1998 | Minshull et al. |
| 5,866,363 A | 2/1999 | Pieczenik |
| 5,885,577 A | 3/1999 | Alvarez |
| 5,885,827 A | 3/1999 | Wabl et al. |
| 5,932,419 A | 8/1999 | Bauer et al. |
| 5,945,329 A | 8/1999 | Breddam et al. |
| 5,965,408 A | 10/1999 | Short |
| 5,976,862 A | 11/1999 | Kauffman et al. |
| 6,004,788 A | 12/1999 | Short |
| 6,054,267 A | 4/2000 | Short |
| 6,057,103 A | 5/2000 | Short |
| 6,171,820 B1 | 1/2001 | Short |
| 6,238,884 B1 | 5/2001 | Short et al. |
| 6,335,179 B1 * | 1/2002 | Short .................... 435/69.1 |
| 6,352,842 B1 | 3/2002 | Short et al. |
| 6,358,709 B1 | 3/2002 | Short et al. |
| 6,361,974 B1 | 3/2002 | Short et al. |

FOREIGN PATENT DOCUMENTS

| | | |
|---|---|---|
| WO | WO 95/20039 | 7/1995 |
| WO | WO 95/22625 | 8/1995 |
| WO | WO 96/06188 | 2/1996 |
| WO | WO 96/09411 | 3/1996 |
| WO | WO 96/41865 | 12/1996 |
| WO | WO 97/20078 | 6/1997 |
| WO | WO 97/20950 | 6/1997 |
| WO | WO 97/35957 | 10/1997 |
| WO | WO 98/01581 | 1/1998 |
| WO | WO 98/13487 | 4/1998 |
| WO | WO 98/27230 | 6/1998 |
| WO | WO 98/32845 | 7/1998 |
| WO | WO 98/38297 | 9/1998 |
| WO | WO 98/42832 | 10/1998 |
| WO | WO 98/45331 | 10/1998 |
| WO | WO 98/48024 | 10/1998 |
| WO | WO 98/49286 | 11/1998 |
| WO | WO 98/58080 | 12/1998 |
| WO | WO 99/36553 | 7/1999 |
| WO | WO 00/52146 | 9/2000 |
| WO | WO 00/52153 | 9/2000 |
| WO | WO 00/52155 | 9/2000 |
| WO | WO 00/52180 | 9/2000 |
| WO | WO 01/30998 A1 | 5/2001 |
| WO | WO 01/31035 A2 | 5/2001 |
| WO | WO 01/31049 A2 | 5/2001 |
| WO | WO 01/42455 A1 | 6/2001 |

OTHER PUBLICATIONS

Cwirla et al., "Peptide on a phage: a vast library of peptides for identifying ligands," *Proc Natl Acad Sci USA* 87(16): 6378–6382 (Aug. 1990).

Delagrave and Youvan, "Searching Sequence Space to Engineer Proteins: Exponential Ensemble Mitagenesis," *Bio/Technology*, 11:1548–1552 (Dec. 1993).

Dennis and Lazarus, "Kunitz domain inhibitors of tissue factor–factor Vlla. I. Potent inhibitors selected from libraries by phage display," *J Biol Chem* 269(35): 22129–22136 (Sep. 2, 1994).

Derbyshire et al., "A Simple and efficient procedure for saturation mutagenesis using mixed oligodeoxynucleotides," *Gene* 46(2–3): 145–152 (1986).

Goff et al., "Efficient saturation mutagenesis of a pentapeptide coding sequence using mixed oligonucleotides," *DNA* 6(4): 381–388 (Aug. 1987).

Hill and Struhl, "Mutagenesis with degenerate oligonucleotides: and efficient method for saturating a defined DNA region with base pair substitutions," *Methods Enzymol* 155:558–568 (1987).

Horwitz and DiMaio, "Saturation mutagenesis using mixed oligonucleotides and M13 templates containing uracil," *Methods Enzymol* 185: 599–611 (1990).

Ihara et al., Requirement of the Pro–Cys–His–Arg sequence for $O^6$–methylguanine DNA methylransferase activity revealed by saturation mutagenesis with negative and positive screening, *Mol Gen Genet* 243(4): 379–389 (May 25, 1994).

J.W. Little, "Saturation mutagenesis of specific codons: elimination of molecule with stop codons from mixed pools of DNA," *Gene* 88(1): 113–115 (Mar. 30, 1990).

Morris and McIvor, "Saturation mutagenesis at dihydrofolate reductase codons 22 and 31. A variety of amino acid substitutions conferring methotrexate resistance," *Biochem Pharmacol* 47(7): 1207–1220 (Mar. 29, 1994).

Olesen and Kielland–Brandt, "Altering substrate preference of carboxypeptidase Y by a novel strategy of mutagenesis eliminating wild type backgroun, " *Protein Eng* 6(4): 409–415 (Jun. 1993).

Olins et al., "Saturation mutagenesis of human interleukin–3," *J Biol Chem* 270(40): pp 23754–123760 (Oct. 6, 1995).

Oliphant and Struhl, "An efficient method for generation proteins with altered enzymatic properties: application to beta–lactamase," *Proc Natl Acad Sci USA* 88(23):9094–9098 (Dec. 1989).

Oliphant et al., "Cloning of random–sequence oligodeoxynucleotides," *Gene* 44 (2–3): 177–183 (1986).

Osuna et al., "combinatorial mutagenesis of three major groove–contacting residues of EcoRI: single and double amino acid replacements retaining methyltransferase–sensative activities," 016(1):7–12 (Sep. 30, 1991).

Reldhaar–Olson et al., "Random mutagenesis of protein sequences using oligonucleotide cassettes," *Methods Enzymol* 208: 564–586 (1991).

Roberts et al., "Directed evolution of a protein: selection of potent neutrophil elastase inhibitors displayed on M13 fusion phage," *Proc Natl Acad Sci USA* 89(6):2433–2433 (Mar. 15, 1992).

Sherman et al., "Saturation mutagenesis of the plasminogen acitibator Inhibitor–1 reactive center," *J Biol Chem* 267(11): 7588–7595 (Apr. 15, 1992).

Singh et al., "Saturation mutagenesis of the octopine synthase enhancer: correlation of mutant pgenotypes with binding of a nuclear protein factor," *Proc Natl Acad Sci USA* 86(10): 3733–3737 (May 1989).

K. Sirotkin, "Advantages to mutagenesis techniques generated populations containing the complete spectrum, of single codon changes," *J. Thsor Biol* 123(3):261–279 (Dec. 7, 1986).

K. Sirotkin, "A computer program to display codon changes caused by a mutagenesis," *Comput Appl Biosci* 4(2):243–247 (Apr. 1988).

K. Sirotkin, "Advantages to mutagenesis techniques generated populations containing the complete spectrum, of single codon changes," *J Theor Biol* 123(3): 261–279 (Dec. 7, 1986).

Soteropoulos and Perlin, "Genetic probing of the stalk segments associated with M2 and M3 of the plasma membrane H+ –ATPase from *Saccharomyces cerevisiae*," *J Biol Chem* 273(41): 26426–26431 (Oct. 9, 1998).

Soteropoulos et al., "Molecular genetic probing of energy coupling by the yeast plasma membrane proton pump," *Acta Physiol Scand* 643: 115–122 (Aug. 19998).

Tsiang et al., "Proteing engineering tyhrombin for optimal specificity and potency of anticoagulant activity in vivo, " *Biochemistry* 35(51): 16449–16457 (Dec. 24, 1996).

Warren et al., "A rapid screen of active site mutants in glycinamide ribonucleotide transformylase," *Biochemistry* 35(27): 8855–8862 (Jul. 9, 1996).

Weiner et al., "A method for the site–directed mono– and multi–mutagenesis of double stranded DNA," *Gene* 126(1): 35–41 (Apr. 15, 1993).

Wells et al., "Cassette mutagenesis: an efficient method for generation of multiple mutations at defined sites," *Gene* 34(2–3): 315–323 (1985).

White et al., "Improved thermostability of the North American firefly luciferase: saturation mutagenesis at position 354," *Biochem*.

Yelton ey al., "Affinity maturation of the BR96 anti–carcinoma antibody by codon–based mutagenesis," *J Immunol* 155(4): 1994–2004 (Aug. 15, 1995).

Zilliacus et al., "Evolution of distinct DNA–binding specificities within the nuclear receptor family of transcription factors," *Proc Natl Acad Sci USA* 91(10); 4175–4179 (May 10, 1994).

Cadwell and Joyce, "Randomization of Genes by PCR Mutagenesis," *Research*, 2:28–33 (1992).

Crameri et al., "Construction and evolution of antibody–phage libraries by DNA shuffling," *Nature Medicine*, 2(1):100–102 (Jan. 1996).

Hermes et al., "Searching sequence space by definably random mutagenesis: Improving the catalytic potency of an enzyme," *Proc. Natl. Acad. Sci. USA.*, 87: 696–700 (Jan. 1990).

Krishnan et al., "Direct and crossover PCR amplification to facilitate Tn5supF–based sequencing of a A phage ciones," *Nucleic Acids Research* 19(22): 6177–1682 (1991).

Marks et al., "By–Passing Immunization: Building High Affinity Human Antibodies by Chain Shuffling," *Bio/Technology* 10:779–783 (Jul. 1992).

Meyerhans et al., "DNA recombination during PCR, " *Nucleic Acids Research* 18(7): 1687–1691.

Moore et al., "Strategies for the in vitro evolution of protein function: enzyme evolution by random recombination of improved sequences," *Journal of Molecular Biology*, 272:336–347 (19971).

Patten et al., Applications of DNA shuffling to pharmaceuticlas and vaccines, *Current Opinion in Biotechnology*, 8(6): 724–733 (1997).

Reidhaar–Olson and Sauer, "Combinatorial Cassette Mutagenesis as a Probe of the Informational Content of Protein Sequences," *Science* 241: 53–57.

George P. Smith, "The progeny of sexual PCR," *Nature*370: 324–325.

Stemmer, "DNA shuffling by random fragmentation and reassembly: In vitro recombination for molecular evolution" *Proceedings of the National Academy of Sciences, USA*, 91: 10747–10752 (Oct. 1994).

Stemmer, "Rapid evolution of a protein in vitro by DNA shuffling," *Nature*, 370: 389–391 (Aug. 4, 1994).

Stemmer et al., "Selection of an Active Single Chain Fv Antibody from a Protein Linker Library Prepared by Enzymatic Inverse PCR, " *BioTechniques* 14(2): 256–265 (1993).

Zhao et al., "Functional and nonfunctional mutations distinguished by random recombination of homologous genes," *Proceedings of the National Academy of Sciences, USA*, 94: 7997–8000 (Jul. 1997).

Zhao et al., "Optimization of DNA shuffling for high fidelity recombination," *Nucleic Acids Research*, 25(6): 1307–1308 (Mar. 15, 1997).

Ge and Rudolph, "Simultaneous Introduction of Multiple Mutations Using Overlap Extensions PCR," *Biotechniques* 22: 28–30 (1997).

Schultz and Richards, "Site saturation studies of β–lactamase: Production and characterization of mutant β—lactamase with all possible amino acid substitutions at residue 71," *Proc. Natl. Acad. Sci. USA*. 83: 1588–1592.

Riechmann and Well, "Phage Display and Selection of Site–Directed Randomized Single–Chain Antibody Fv Frahment for Its Affinity Improvement," *Biochemistry* 32: 8848–8855.

Zhao et al., "Molecular evolution by staggered extension process (StEP) in vitro recombination," *Nature Biotechnology* 16:258–261 (1998).

Cwirla, Steven E. et al., "Peptides on Phage: A Vast Library of Peptides for Identifying Ligands," *Proc. Natl. Acad. Sci. USA*, vol. 87, Aug. 1990, pp. 6378–6382.

Hill, David E. et al., "[34] Mutagenesis with Degenerate Oligonucleotides: An Efficient Method for Saturating a Defined DNA Region with Base Pair Substitutions," *Methods in Enzymology*, vol. 155, 1987, pp. 558–569.

Murray, Richard et al., "Saturation Mutagenesis of a Major Histocompatibility Complex Protein Domain: Indetification of a Single Conserved Amino Acid Important for Allorecognition," *Proc. Natl. Acad. Sci, USA*, vol. 85., May 1988, pp. 3535–3539.

Dube et al., Artificial mutants generated by a the insertion of random oligonucieotides into the putative nculeoside binding site of the HSV–1 thymidine kinase gene, *Biochemistry*, 1991, vol. 30. pp. 11760–11767.

Burioni et al., Engineering human monoclonal antibody fragments: A recombinant enzyme–linked Fab. *Microbiologica*, Apr. 1995, vol. 18, pp. 127–133.

Borrego et al., Combinatorial libraries by cassette mutagenesis, Nucleic Acid Research, 1995, vol. 23, No. 10 pp. 1834–1835.

Kubo et al., Alteration of Specific Activity and Stability of Thermostable Neutral Proetease by Site–Directed Mutagenesis, Appl. Envrion, Microbiol., vol. 58, No. 11, pp. 3779–3783, see p. 3779, second paragraph 1992.

Osuna et al., Combinatorial mutagenesis of three major groove–contacting residues of EcoRI: single and double amino acid replacements retaining metyltransferase–sensitive activity, *Gene*. 1991, vol. 106 pp. 7–12.

Dube et al., Artificial mutants generated by the insertion of random oligonucieotides into the putative nucleoside binding site of the HSV–1 thymidine kinase gene, *Biochemistry*, 1991, vol. 30, pp. 11760–11767.

Burioni et al., Engineering human monoclonal antibody fragments: A recombinant enzyme–linked Fab. *Microbiologica*, Apr. 1995, vol. 18, pp. 127–133.

Borrego et al., Combinatorial libraries by cassette mutagenesis, *Nucleic Acid Research*, 1995, vol. 23, No. 10 pp. 1834–1835.

Kubo et al., Alteration of Specific Activity and Stability of Thermostable Neutral Proetease by Site–Directed Mutagenesis, Appl. Environ. Micobiol., vol. 58, No. 11, pp. 3779–3783, see p. 3779, second paragraph.

* cited by examiner

```
1    ATG CTA CCA GAA GGC TTT CTC TGG GGC GTG TCC CAG TCC GGC TTT CAG TTC GAG ATG GGC   60
1    Met Leu Pro Glu Gly Phe Leu Trp Gly Val Ser Gln Ser Gly Phe Gln Phe Glu Met Gly   20

61   GAC AAG CTC AGG AGG AAC ATT GAT CCG AAC ACA GAC TGG AAG TGG GTC GAT CCC          120
21   Asp Lys Leu Arg Arg Asn Ile Asp Pro Asn Thr Asp Trp Lys Trp Val Arg Asp Pro      40

121  TTC AAC ATA AAG AGG GAA CTC GTC AGC GAC CTG CCC GAG ATA GAG AAC GGG ATA AAC TAC  180
41   Phe Asn Ile Lys Arg Glu Leu Val Ser Gly Asp Leu Pro Glu Ile Glu Asn Gly Ile Asn Tyr 60

181  GAA CTT TAC GAG AAG GAT CAC CCC CTC GCC AGA GAC CTG GGT CTG AAC GTT TAC AGG ATT  240
61   Glu Leu Tyr Glu Lys Asp His Pro Leu Ala Arg Asp Leu Gly Leu Asn Val Tyr Arg Ile  80

241  GGA ATA GAG TGG AGC AGG ATC TTT CCC CCA ACC TGG CCA ACC TTT GTG GAC GTT GAA      300
81   Gly Ile Glu Trp Ser Arg Ile Phe Pro Pro Thr Trp Pro Thr Phe Val Asp Val Glu      100

301  CGG GAC AGC TAC GGA AAT CAT CAG GAG ATA GCC TAC GTT AAA GAC GTC CGC GAA GAG CTC  360
101  Arg Asp Ser Tyr Gly Asn His Gln Glu Ile Ala Tyr Val Lys Asp Val Arg Glu Glu Leu  120

361  GAC GAG ATA GCG AAT CAT CAG GAG ATA GCC TAC CGC CGT GTT ATA GAG CTC ATC AGG      420
121  Asp Glu Ile Ala Asn His Gln Glu Ile Ala Tyr Arg Arg Val Ile Glu Leu Ile Arg      140

421  GAG CTG GGC TTC AAG GTC ATC GTG AAC CTC AAC CAC TTC ACG CTC CCC CTC TGG CTT CAC  480
141  Glu Leu Gly Phe Lys Val Ile Val Asn Leu Asn His Phe Ghr Leu Pro Leu Trp Leu His  160

481  GAT CCG ATA ATC GCG AGG GAG AAG GCC CTC ACC AAC GGT AGG ATT GGC TGG GTC GGG CAG  540
161  Asp Pro Ile Ile Ala Arg Glu Lys Ala Leu Thr Asn Gly Arg Ile Gly Trp Val Gly Gln  180
```

FIG. 1A

```
541  GAG AGC GTG GTG GAG TTC GCC AAG TAC ATC GCG AAC GCA CTC GGG GAC CTC   600
181  Glu Ser Val Val Glu Phe Ala Lys Tyr Ile Ala Asn Ala Leu Gly Asp Leu  200

601  GTT GAT ATG TGG AGC ACC TTC AAC GAR CCG ATG GTC GTT GTG GAN CTC GCG   660
201  Val Asp Met Trp Ser Thr Phe Asn Glu Pro Met Val Val Xxx Leu Leu Ala  220

661  CCC TAC TCC GGY TTT CCN CCG GGG GTT ATG AAC CCC GAG GCG GMN AAN CTG   720
221  Pro Tyr Ser Gly Phe Pro Pro Gly Val Met Asn Pro Glu Ala Xxx Xxx Leu  240

721  AAC ATA AAC GCC CAC GCA CTG GCC TAC AAG ATG ATA AAG AAG TTC GAC AGG   780
241  Asn Ile Asn Ala His Ala Leu Ala Tyr Lys Met Ile Lys Lys Phe Asp Arg  260

781  GCC GAT AAG GAT TCC CGC TCC GAG GCC ATC ATA TAC GGG ATA ATC GAG ATA   840
261  Ala Asp Lys Asp Ser Arg Ser Glu Ala Ile Ile Tyr Gly Ile Ile Glu Ile  280

841  NCC TAT CCA NAC GAC TCC AAC CCN AAG GAC CTG AAA NCT NCA GAA AAC TAC   900
281  Xxx Tyr Pro Xxx Asp Ser Asn Pro Lys Asp Leu Lys Xxx Xxx Glu Asn Tyr  300

901  TTC CAC AGC GGG CTC TTC TTC GCA ATC CAC CAC AAG GGC AAC ATC GAG TTC   960
301  Phe His Ser Gly Leu Phe Phe Ala Ile His His Lys Gly Asn Ile Glu Phe  320

961  GGT GAG ACC TTC GTC AAA GTT CGG CAT CTC AGG GGG AAC GAC TGG ATA GGC  1020
321  Gly Glu Thr Phe Val Lys Val Arg His Leu Arg Gly Asn Asp Trp Ile Gly  340

1021 TAC ACG AGA GAA GTC GTC AGG TAT TCG GAG CCC AAG TTC CCG AGC ATA CCC  1080
341  Tyr Thr Arg Glu Val Val Arg Tyr Ser Glu Pro Lys Phe Pro Ser Ile Pro  360
```

FIG. 1B

| 1081 | TTC | CGG | GGA | GTT | CAC | AAC | TAC | GCC | TGC | AGG | CCC | GGG | AGT | TCT | TCC | GCC | GAC | GGA | 1140 |
| 361 | Phe | Arg | Gly | Val | His | Asn | Tyr | Ala | Cys | Arg | Pro | Gly | Ser | Ser | Ser | Ala | Asp | Gly | 380 |
| 1141 | AGG | CCC | GTA | AGC | GAC | ATC | GGC | ATC | TAT | CCG | GAG | GGG | ATC | TAC | GAC | TCG | ATA | AGA | 1200 |
| 381 | Arg | Pro | Val | Ser | Asp | Ile | Gly | Ile | Tyr | Pro | Glu | Gly | Ile | Tyr | Asp | Ser | Ile | Arg | 400 |
| 1201 | GAG | GCC | AAC | AAA | TAC | GGG | GTC | CCG | GTT | TAC | GTC | ACC | GAA | AAC | GGA | ATA | GCC | GAT | TCA | ACT | 1260 |
| 401 | Glu | Ala | Asn | Lys | Tyr | Gly | Val | Pro | Val | Tyr | Val | Thr | Glu | Asn | Gly | Ile | Ala | Asp | Ser | Thr | 420 |
| 1261 | GAC | ACC | CTG | CGG | CCG | TAC | TAC | CTC | GCG | AGC | CAT | GTA | GCG | AAG | ATT | GAG | GAG | GCG | TAC | GAG | 1320 |
| 421 | Asp | Thr | Leu | Arg | Pro | Tyr | Tyr | Leu | Ala | Ser | His | Val | Ala | Lys | Ile | Glu | Glu | Ala | Tyr | Glu | 440 |
| 1321 | GCG | GGT | TAC | GAC | GTC | AGG | GGC | CTG | TAC | TGG | GCC | ACC | GAC | CTG | ATA | ACC | AAG | GAG | AGA | ACA | 1380 |
| 441 | Ala | Gly | Tyr | Asp | Val | Arg | Gly | Leu | Tyr | Trp | Ala | Thr | Asp | Leu | Ile | Thr | Lys | Glu | Arg | Thr | 460 |
| 1381 | CTC | GGT | TTC | AGG | ATG | AGG | TTC | GGC | CTC | TAT | AAA | GTG | GAT | CTC | ATA | ACC | AAG | GAG | AGA | ACA | 1440 |
| 461 | Leu | Gly | Phe | Arg | Met | Arg | Phe | Gly | Leu | Tyr | Lys | Val | Asp | Leu | Ile | Thr | Lys | Glu | Arg | Thr | 480 |
| 1441 | CCG | CGG | GAA | GAG | AGC | GTA | AAG | GTT | TAT | AGG | GGC | ATC | GTG | GAG | AAC | AAC | GGA | GTG | AGC | AAG | 1500 |
| 481 | Pro | Arg | Glu | Glu | Ser | Val | Lys | Val | Tyr | Arg | Gly | Ile | Val | Glu | Asn | Asn | Gly | Val | Ser | Lys | 500 |
| 1501 | GAA | ATC | CGG | GAG | AAG | TTC | GGA | CTT | GGG | TGA | 1530 |
| 501 | Glu | Ile | Arg | Glu | Lys | Phe | Gly | Leu | Gly | End | 510 |

FIG. 1C

SEQUENCE LISTING

<160> NUMBER OF SEQ ID NOS: 2

<210> SEQ ID NO 1
<211> LENGTH: 1530
<212> TYPE: DNA
<213> ORGANISM: Thermococcus 9N2 Beta-glycosidase
<220> FEATURE:
<221> NAME/KEY: misc_feature
<222> LOCATION: (1)..(1530)
<223> OTHER INFORMATION: n is any nucleotide
<220> FEATURE:
<221> NAME/KEY: CDS
<222> LOCATION: (1)..(1530)
<223> OTHER INFORMATION:

<400> SEQUENCE: 1

```
atg cta cca gaa ggc ttt ctc tgg ggc gtg tcc cag tcc ggc ttt cag      48
Met Leu Pro Glu Gly Phe Leu Trp Gly Val Ser Gln Ser Gly Phe Gln
1               5                   10                  15 ttc gag atg ggc gac aag ctc agg agg aac att gat ccg aac aca gac      96
Phe Glu Met Gly Asp Lys Leu Arg Arg Asn Ile Asp Pro Asn Thr Asp
            20                  25                  30 tgg tgg aag tgg gtc agg gat ccc ttc aac ata aag agg gaa ctc gtc     144
```

```
Trp Trp Lys Trp Val Arg Asp Pro Phe Asn Ile Lys Arg Glu Leu Val
        35                  40                  45 agc ggc gac ctg ccc gag gag ggg ata aac aac tac gaa ctt tac gag    192
Ser Gly Asp Leu Pro Glu Glu Gly Ile Asn Asn Tyr Glu Leu Tyr Glu
 50                  55                  60 aag gat cac cgc ctc gcc aga gac ctc ggt ctg aac gtt tac agg att    240
Lys Asp His Arg Leu Ala Arg Asp Leu Gly Leu Asn Val Tyr Arg Ile
 65              70                  75                  80 gga ata gag tgg agc agg atc ttt ccc tgg cca acg tgg ttt gtg gag    288
Gly Ile Glu Trp Ser Arg Ile Phe Pro Trp Pro Thr Trp Phe Val Glu
                 85                  90                  95 gtt gac gtt gag cgg gac agc tac gga ctc gtg aag gac gtc aaa atc    336
Val Asp Val Glu Arg Asp Ser Tyr Gly Leu Val Lys Asp Val Lys Ile
                100                 105                 110 gat aaa gac acg ctc gaa gag ctc gac gag ata gcg aat cat cag gag    384
Asp Lys Asp Thr Leu Glu Glu Leu Asp Glu Ile Ala Asn His Gln Glu
            115                 120                 125 ata gcc tac tac cgc cgc gtt ata gag cac ctc agg gag ctg ggc ttc    432
Ile Ala Tyr Tyr Arg Arg Val Ile Glu His Leu Arg Glu Leu Gly Phe
        130                 135                 140 aag gtc atc gtg aac ctc aac cac ttc acg ctc ccc ctc tgg ctt cac    480
Lys Val Ile Val Asn Leu Asn His Phe Thr Leu Pro Leu Trp Leu His
145                 150                 155                 160 gat ccg ata atc gcg agg gag aag gcc ctc acc aac ggt agg att ggc    528
Asp Pro Ile Ile Ala Arg Glu Lys Ala Leu Thr Asn Gly Arg Ile Gly
                165                 170                 175 tgg gtc ggg cag gag agc gtg gtg gag ttc gcc aag tac gcg gcg tac    576
Trp Val Gly Gln Glu Ser Val Val Glu Phe Ala Lys Tyr Ala Ala Tyr
                180                 185                 190 atc gcg aac gca ctc ggg gac ctc gtt gat atg tgg agc acc ttc aac    624
Ile Ala Asn Ala Leu Gly Asp Leu Val Asp Met Trp Ser Thr Phe Asn
        195                 200                 205 gag ccg atg gtc gtt gtg gan ctc ggt tac ctc gcg ccc tac tcc ggy    672
Glu Pro Met Val Val Val Xaa Leu Gly Tyr Leu Ala Pro Tyr Ser Gly
    210                 215                 220 ttt ccn ccg ggg gtt atg aac ccc gag gcg gmn aan ctg gca atc ctc    720
Phe Pro Pro Gly Val Met Asn Pro Glu Ala Xaa Xaa Leu Ala Ile Leu
225                 230                 235                 240 aac atg ata aac gcc cac gca ctg gcc tac aag atg ata aag aag ttc    768
Asn Met Ile Asn Ala His Ala Leu Ala Tyr Lys Met Ile Lys Lys Phe
                245                 250                 255 gac agg gta aag gcc gat aag gat tcc cgc tcc gag gcc gag gtc ggg    816
Asp Arg Val Lys Ala Asp Lys Asp Ser Arg Ser Glu Ala Glu Val Gly
                260                 265                 270 ata atc tac aac aac ata ggc gtt ncc tat cca nac gac tcc aac gac    864
Ile Ile Tyr Asn Asn Ile Gly Val Xaa Tyr Pro Xaa Asp Ser Asn Asp
        275                 280                 285 ccn aag gac ctg aaa nct nca gaa aac gac aac tac ttc cac agc ggg    912
Pro Lys Asp Leu Lys Xaa Xaa Glu Asn Asp Asn Tyr Phe His Ser Gly
    290                 295                 300 ctc ttc ttc gac gca atc cac aag ggc aag ctc aac atc gag ttc gac    960
Leu Phe Phe Asp Ala Ile His Lys Gly Lys Leu Asn Ile Glu Phe Asp
305                 310                 315                 320 ggt gag acc ttc gtc aaa gtt cgg cat ctc agg ggg aac gac tgg ata   1008
Gly Glu Thr Phe Val Lys Val Arg His Leu Arg Gly Asn Asp Trp Ile
                325                 330                 335 ggc gtt aac tac tac acg aga gaa gtc gtc agg tat tcg gag ccc aag   1056
Gly Val Asn Tyr Tyr Thr Arg Glu Val Val Arg Tyr Ser Glu Pro Lys
        340                 345                 350
```

```
ttc ccg agc ata ccc ctg ata tcc ttc cgg gga gtt cac aac tac ggc      1104
Phe Pro Ser Ile Pro Leu Ile Ser Phe Arg Gly Val His Asn Tyr Gly
        355                 360                 365 tac gcc tgc agg ccc ggg agt tct tcc gcc gac gga agg ccc gta agc      1152
Tyr Ala Cys Arg Pro Gly Ser Ser Ser Ala Asp Gly Arg Pro Val Ser
    370                 375                 380 gac atc ggc tgg gag atc tat ccg gag ggg atc tac gac tcg ata aga      1200
Asp Ile Gly Trp Glu Ile Tyr Pro Glu Gly Ile Tyr Asp Ser Ile Arg
385                 390                 395                 400 gag gcc aac aaa tac ggg gtc ccg gtt tac gtc acc gaa aac gga ata      1248
Glu Ala Asn Lys Tyr Gly Val Pro Val Tyr Val Thr Glu Asn Gly Ile
                405                 410                 415 gcc gat tca act gac acc ctg cgg ccg tac tac ctc gcg agc cat gta      1296
Ala Asp Ser Thr Asp Thr Leu Arg Pro Tyr Tyr Leu Ala Ser His Val
            420                 425                 430 gcg aag att gag gag gcg tac gag gcg ggt tac gac gtc agg ggc tac      1344
Ala Lys Ile Glu Glu Ala Tyr Glu Ala Gly Tyr Asp Val Arg Gly Tyr
        435                 440                 445 ctc tac tgg gcg ctg acc gac aac tac gag tgg gcc ctc ggt ttc agg      1392
Leu Tyr Trp Ala Leu Thr Asp Asn Tyr Glu Trp Ala Leu Gly Phe Arg
    450                 455                 460 atg agg ttc ggc ctc tat aaa gtg gat ctc ata acc aag gag aga aca      1440
Met Arg Phe Gly Leu Tyr Lys Val Asp Leu Ile Thr Lys Glu Arg Thr
465                 470                 475                 480 ccg cgg gag gaa agc gta aag gtt tat agg ggc atc gtg gag aac aac      1488
Pro Arg Glu Glu Ser Val Lys Val Tyr Arg Gly Ile Val Glu Asn Asn
                485                 490                 495 gga gtg agc aag gaa atc cgg gag aag ttc gga ctt ggg tga              1530
Gly Val Ser Lys Glu Ile Arg Glu Lys Phe Gly Leu Gly
            500                 505

<210> SEQ ID NO 2
<211> LENGTH: 509
<212> TYPE: PRT
<213> ORGANISM: Thermococcus 9N2 Beta-glycosidase
<220> FEATURE:
<221> NAME/KEY: misc_feature
<222> LOCATION: (215)..(215)
<223> OTHER INFORMATION: The 'Xaa' at location 215 stands for Glu, or
      Asp.
<220> FEATURE:
<221> NAME/KEY: misc_feature
<222> LOCATION: (224)..(224)
<223> OTHER INFORMATION: The 'Xaa' at location 224 stands for Gly.
<220> FEATURE:
<221> NAME/KEY: misc_feature
<222> LOCATION: (235)..(235)
<223> OTHER INFORMATION: The 'Xaa' at location 235 stands for Glu,
      Asp, or Ala.
<220> FEATURE:
<221> NAME/KEY: misc_feature
<222> LOCATION: (236)..(236)
<223> OTHER INFORMATION: The 'Xaa' at location 236 stands for Lys, or
      Asn.
<220> FEATURE:
<221> NAME/KEY: misc_feature
<222> LOCATION: (281)..(281)
<223> OTHER INFORMATION: The 'Xaa' at location 281 stands for Thr, Ala,
      Pro, or Ser.
<220> FEATURE:
<221> NAME/KEY: misc_feature
<222> LOCATION: (284)..(284)
<223> OTHER INFORMATION: The 'Xaa' at location 284 stands for Asn, Asp,
      His, or Tyr.
<220> FEATURE:
<221> NAME/KEY: misc_feature
<222> LOCATION: (294)..(294)
<223> OTHER INFORMATION: The 'Xaa' at location 294 stands for Thr, Ala,
      Pro, or Ser.
```

```
<220> FEATURE:
<221> NAME/KEY: misc_feature
<222> LOCATION: (295)..(295)
<223> OTHER INFORMATION: The 'Xaa' at location 295 stands for Thr, Ala,
      Pro, or Ser.

<400> SEQUENCE: 2

Met Leu Pro Glu Gly Phe Leu Trp Gly Val Ser Gln Ser Gly Phe Gln
1               5                   10                  15

Phe Glu Met Gly Asp Lys Leu Arg Arg Asn Ile Asp Pro Asn Thr Asp
            20                  25                  30

Trp Trp Lys Trp Val Arg Asp Pro Phe Asn Ile Lys Arg Glu Leu Val
        35                  40                  45

Ser Gly Asp Leu Pro Glu Glu Gly Ile Asn Asn Tyr Glu Leu Tyr Glu
    50                  55                  60

Lys Asp His Arg Leu Ala Arg Asp Leu Gly Leu Asn Val Tyr Arg Ile
65                  70                  75                  80

Gly Ile Glu Trp Ser Arg Ile Phe Pro Trp Pro Thr Trp Phe Val Glu
                85                  90                  95

Val Asp Val Glu Arg Asp Ser Tyr Gly Leu Val Lys Asp Val Lys Ile
            100                 105                 110

Asp Lys Asp Thr Leu Glu Glu Leu Asp Glu Ile Ala Asn His Gln Glu
        115                 120                 125

Ile Ala Tyr Tyr Arg Arg Val Ile Glu His Leu Arg Glu Leu Gly Phe
130                 135                 140

Lys Val Ile Val Asn Leu Asn His Phe Thr Leu Pro Leu Trp Leu His
145                 150                 155                 160

Asp Pro Ile Ile Ala Arg Glu Lys Ala Leu Thr Asn Gly Arg Ile Gly
                165                 170                 175

Trp Val Gly Gln Glu Ser Val Val Glu Phe Ala Lys Tyr Ala Ala Tyr
            180                 185                 190

Ile Ala Asn Ala Leu Gly Asp Leu Val Asp Met Trp Ser Thr Phe Asn
        195                 200                 205

Glu Pro Met Val Val Val Xaa Leu Gly Tyr Leu Ala Pro Tyr Ser Xaa
    210                 215                 220

Phe Pro Pro Gly Val Met Asn Pro Glu Ala Xaa Xaa Leu Ala Ile Leu
225                 230                 235                 240

Asn Met Ile Asn Ala His Ala Leu Ala Tyr Lys Met Ile Lys Lys Phe
                245                 250                 255

Asp Arg Val Lys Ala Asp Lys Asp Ser Arg Ser Glu Ala Glu Val Gly
            260                 265                 270

Ile Ile Tyr Asn Asn Ile Gly Val Xaa Tyr Pro Xaa Asp Ser Asn Asp
        275                 280                 285

Pro Lys Asp Leu Lys Xaa Xaa Glu Asn Asp Asn Tyr Phe His Ser Gly
    290                 295                 300

Leu Phe Phe Asp Ala Ile His Lys Gly Lys Leu Asn Ile Glu Phe Asp
305                 310                 315                 320

Gly Glu Thr Phe Val Lys Val Arg His Leu Arg Gly Asn Asp Trp Ile
                325                 330                 335

Gly Val Asn Tyr Tyr Thr Arg Glu Val Val Arg Tyr Ser Glu Pro Lys
            340                 345                 350

Phe Pro Ser Ile Pro Leu Ile Ser Phe Arg Gly Val His Asn Tyr Gly
        355                 360                 365

Tyr Ala Cys Arg Pro Gly Ser Ser Ala Asp Gly Arg Pro Val Ser
370                 375                 380
```

-continued

```
Asp Ile Gly Trp Glu Ile Tyr Pro Glu Gly Ile Tyr Asp Ser Ile Arg
385                 390                 395                 400

Glu Ala Asn Lys Tyr Gly Val Pro Val Tyr Val Thr Glu Asn Gly Ile
            405                 410                 415

Ala Asp Ser Thr Asp Thr Leu Arg Pro Tyr Tyr Leu Ala Ser His Val
            420                 425                 430

Ala Lys Ile Glu Glu Ala Tyr Glu Ala Gly Tyr Asp Val Arg Gly Tyr
            435                 440                 445

Leu Tyr Trp Ala Leu Thr Asp Asn Tyr Glu Trp Ala Leu Gly Phe Arg
    450                 455                 460

Met Arg Phe Gly Leu Tyr Lys Val Asp Leu Ile Thr Lys Glu Arg Thr
465                 470                 475                 480

Pro Arg Glu Glu Ser Val Lys Val Tyr Arg Gly Ile Val Glu Asn Asn
                485                 490                 495

Gly Val Ser Lys Glu Ile Arg Glu Lys Phe Gly Leu Gly
                500                 505
```

DIRECTED EVOLUTION OF THERMOPHILIC ENZYMES

This application is a continuation of application U.S. Ser. No. 09/185,373, filed Nov. 3, 1998, now U.S. Pat. No. 6,335,179, which is a continuation of application U.S. Ser. No. 08/760,489, filed Dec. 5, 1996, now U.S. Pat. No. 5,830,696, and claims benefit of application U.S. Ser. No. 60/008,311, filed Dec. 7, 1995, now abandoned.

The present invention relates to enzymes, particularly to thermostable enzymes. More particularly, the present invention relates to thermostable enzymes which are stable at high temperature and which have improved activity at lower temperatures.

Thermostable enzymes are enzymes that function at greater than 60° C. Thermostable enzymes are utilized in both industry and biomedical research in assays where certain steps of the assay are performed at significantly increased temperatures. Thermostable enzymes may be obtained from thermophilic organisms found in hot springs, volcanic origin, tropical areas etc. Examples of such organisms, for instance, include prokaryotic microorganisms, such as eubacteria and archaebacteria (Bronneomerier, K. and Staudenbauer, W. L., D. R. Woods (ed), the Clostridia and Biotechnology, Butterworth Publishers, Stoneham, M. A. (1993), among other organisms.

Thermostable enzymes exhibit greater storage life capacity and organic solvent resistance, as compared to their mesophilic counterparts.

There are applications in industry and in research for thermostable enzymes which exhibit enzyme activity at a desired minimum temperature. An example of this occurs in molecular diagnostics wherein reporter molecules must survive long term storage at room temperature or higher or they need to function in unusual environments, and the assays which employ them are performed at room temperature where the activity of thermostable enzymes is generally very low.

FIG. 1 illustrates the full length DNA sequence and corresponding deduced amino acid sequence of Thermococcus 9N2 Beta-glycosidase.

Applicant has found that it is possible to provide thermostable enzymes which have improved activity at lower temperatures.

More particularly, Applicant has found that the activity of thermophilic enzymes can be improved at lower temperatures while maintaining the temperature stability of such enzymes.

Still more particularly, Applicant has found there can be obtained a thermostable enzyme with improved activity at lower temperature by subjecting to mutagenesis a thermostable enzyme or polynucleotide encoding such thermostable enzyme followed by a screening of the resulting mutants to identify a mutated enzyme or a mutated polynucleotide encoding a mutated enzyme, which mutated enzyme retains thermostability and which has an enzyme activity at lower temperatures which is at least two (2) times greater than a corresponding non-mutated enzyme.

The thermostable enzymes and mutated thermostable enzymes are stable at temperatures up to 60° C. and preferably are stable at temperatures of up to 70° C. and more preferably at temperatures up to 95° C. and higher.

Increased activity of mutated thermostable enzymes at lower temperatures is meant to encompass activities which are at least two-fold, preferably at least four-fold, and more preferably at least ten-fold greater than that of the corresponding wild-type enzyme.

Increased enzyme activity at lower temperatures means that enzyme activity is increased at a temperature below 50° C., preferably below 40° C. and more preferably below 30° C. Thus, in comparing enzyme activity at a lower temperature between the mutated and non-mutated enzyme, the enzyme activity of the mutated enzyme at defined lower temperatures is at least 2 times greater than the enzyme activity of the corresponding non-mutated enzyme.

Thus, lower temperatures and lower temperature ranges include temperatures which are at least 5° C. less than the temperature at which thermostable enzymes are stable, which includes temperatures below 55° C., 50° C., 45° C., 40° C., 35° C., 30° C., 25° C. and 20° C., with below 50° C. being preferred, and below 40 being more preferred, and below 30° C. (or approximately room temperature) being most preferred.

In accordance with an aspect of the present invention, the lower temperature or lower temperature range at which a greater enzyme activity is desired is determined and a thermostable enzyme(s), or polynucleotide encoding such enzyme(s), are subjected to mutagenesis and the resulting mutants are screened to determine mutated enzymes (or polynucleotide encoding mutated enzymes) which retain thermostability and which have a minimum desired increase in enzyme activity at the desired temperature or temperature range.

Thermostable enzymes are enzymes which have activity, i.e. are not degraded, at temperatures above 60° C. Thermostable enzymes also have increased storage life, and high resistance to organic solvents.

Thermostable enzymes may be isolated from thermophilic organisms such as those which are found in elevated temperatures such as in hot springs, volcanic areas and tropical areas. Examples of thermophilic organisms are prokaryotic organisms for example, thermophilic bacteria such as eubacteria and archaebacteria.

The DNA from these thermostable organisms can then be isolated by available techniques that are described in the literature. The IsoQuick® nucleic acid extraction kit (MicroProbe Corporation) is suitable for this purpose.

The term "derived" or "isolated" means that material is removed from its original environment (e.g., the natural environment if it is naturally occurring). For example, a naturally-occurring polynucleotide or polypeptide present in a living animal is not isolated, but the same polynucleotide or polypeptide separated from some or all of the coexisting materials in the natural system, is isolated.

The DNA isolated or derived from these microorganisms can preferably be inserted into a vector. Such vectors are preferably those containing expression regulatory sequences, including promoters, enhancers and the like. Such polynucleotides can be part of a vector and/or a composition and still be isolated, in that such vector or composition is not part of its natural environment.

Alternatively, enzymes not known to have thermostable properties can be screened for such properties by inserting the DNA encoding the enzyme in an expression vector and transforming a suitable host as hereinafter described, such that the enzyme may be expressed and screened for positive thermostable activity.

As representative examples of expression vectors which may be used there may be mentioned viral particles, baculovirus, phage, plasmids, phagemids, cosmids, phosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus, yeast, etc.) Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE70, pQE60, pQE-9 (Qiagen), psiX174, pBluescript SK, pBluescript KS, (Stratagene); pTRC99a, pKK223-3, pKK233-3, pDR540, pRIT2T (Pharmacia); Eukaryotic: pWLNEO, pXT1, pSG (Stratagene) pSVK3, pBPV, pMSG, pSVLSV40 (Pharmacia). Any other plasmid or vector may be used as long as they are replicable and viable in the host.

The DNA derived from a microorganism(s) may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence (s) (promoter) to direct mRNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operon encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the peroplasmic space or extracellular medium.

The DNA selected and isolated as hereinabove described is introduced into a suitable host to prepare a library which is screened for the desired enzyme activity. The selected DNA is preferably already in a vector which includes appropriate control sequences whereby selected DNA which encodes for an enzyme may be expressed, for detection of the desired activity. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by transformation, calcium phosphate transfection, DEAE-Dextran mediated transfection, or electroporation (Davis, L., Dibner, M., Battey, I., Basic Methods in Molecular Biology, (1986)).

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa 293 and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells are genetically engineered (transduced or transformed or transfected) with the vectors. The engineered host cells can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan.

The isolated DNA encoding a thermostable enzyme is subjected to mutagenesis techniques, with the preferred type of mutagenesis techniques being set forth below.

The term "error-prone PCR" refers to a process for performing PCR under conditions where the copying fidelity of the DNA polymerase is low, such that a high rate of point mutations is obtained along the entire length of the PCR product. Leung, D. W., et al., Technique, 1:11–15 (1989) and Caldwell, R. C. & Joyce G. F., PCR Methods Applic., 2:28–33 (1992).

The term "oligonucleotide directed mutagenesis" refers to a process which allows for the generation of site-specific mutations in any cloned DNA segment of interest. Reidhaar-Olson, J. F. & Sauer, R. T., et al., Science, 241:53–57 (1988).

The term "assembly PCR" refers to a process which involves the assembly of a PCR product from a mixture of small DNA fragments. A large number of different PCR reactions occur in parallel in the same vial, with the products of one reaction priming the products of another reaction.

The term "sexual PCR mutagenesis" refers to forced homologous recombination between DNA molecules of different but highly related DNA sequence in vitro, caused by random fragmentation of the DNA molecule based on sequence homology, followed by fixation of the crossover by primer extension in a PCR reaction. Stemmer, W. P., PNAS, USA, 91:10747–10751 (1994).

The term "in vivo mutagenesis" refers to a process of generating random mutations in any cloned DNA of interest which involves the propagation of the DNA in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA.

The term "cassette mutagenesis" refers to any process for replacing a small region of a double stranded DNA molecule with a synthetic oligonucleotide "cassette" that differs from the native sequence. The oligonucleotide often contains completely and/or partially randomized native sequence.

The term "recursive ensemble mutagenesis" refers to an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Arkin, A. P. and Youvan, D.C., PNAS, USA, 89:7811–7815 (1992).

The term "exponential ensemble mutagenesis" refers to a process for generating combinatorial libraries with a high percentage of unique and functional mutants, wherein small groups of residues are randomized in parallel to identify, at each altered position, amino acids which lead to functional proteins, Delegrave, S. and Youvan, D.C., Biotechnology Research, 11:1548–1552 (1993); and random and site-directed mutagenesis, Arnold, F. H., Current Opinion in Biotechnology, 4:450–455 (1993). All of the references mentioned above are hereby incorporated by reference in their entirety.

As can be seen from the above mutagenesis techniques, the DNA encoding an enzyme having the desired activity may be subject to mutagenesis alone, i.e. as naked DNA, or the DNA may be subjected to mutagenesis after insertion into an appropriate vector as hereinabove described. These techniques are referred to as in vitro mutagenesis.

Alternatively, in vivo mutagenesis may be performed wherein the DNA is subjected to mutagenesis while it is within a cell or living organism. A preferred example of this technique utilizes the XL1 Red Strain of E. Coli (Stratagene, Inc.) which has its DNA repair genes, MutH, MutL and MutS, deleted such that many different mutations occur in a short time. Up to 10,000 mutations may take place within a 30 hour time span such that an entire mutated DNA library may be prepared from mutated DNA by procedures known in the art.

After an appropriate amount of time to allow mutations to take place, the mutated DNA is excised from the host cell in the case of in vivo mutagenesis and inserted in another appropriate vector and used to transform a non-mutator host, for example, XL1 Blue strain of E. Coli after which a mutated DNA library is prepared. In the case of in vitro mutagenesis, if the mutated DNA has previously been inserted in an appropriate expression vector, said vector is then used directly to transform an appropriate non-mutator host for the preparation of a mutated DNA library, if the mutagenized DNA is not in an appropriate expression vector.

A library is prepared for screening by transforming a suitable organism. Hosts, particularly those specifically identified herein as preferred, are transformed by artificial introduction of the vectors containing the mutated DNA by inoculation under conditions conducive for such transformation.

The resultant libraries of transformed clones are then screened for clones which display activity for the enzyme of interest in a phenotypic assay for enzyme activity.

For example, having prepared a multiplicity of clones from DNA mutagenized by one of the techniques described above, such clones are screened for the specific enzyme activity of interest.

For example, the clones containing the mutated DNA are now subject to screening procedures to determine their activity within both higher temperatures and within the desired lower temperature range to identify mutants which have the desired increase in activity within the lower temperature range when compared to the corresponding wild-type thermostable enzyme which is non-mutated.

Positively identified clones, i.e. those which contain mutated DNA sequences which express thermostable enzymes which are thermostable and yet have an increased activity at least two times than the corresponding wild-type enzyme at temperatures within the lower temperature range, are isolated and sequenced to identify the DNA sequence. As an example, phosphatase activity at the desired lower temperature ranges may be identified by exposing the clones, and thus the thermostable enzyme and testing its ability to cleave an appropriate substrate.

In Example 1 phosphatase and β-galactosidase activity are measured by comparing the wild-type enzymes to the enzymes subjected to mutagenesis. As can be seen from the results of Example 1, mutagenesis of a wild-type phosphatase and β-galactosidase thermophilic enzyme produce mutated enzymes which were 3 and 2.5 times more active, respectively, at lower temperatures than the corresponding wild-type enzymes within the lower temperature range of room temperature.

In the case of protein engineering, after subjecting a thermophilic enzyme to mutagenesis, the mutagenized enzyme is screened for the desired activity namely, increased activity at lower temperatures while maintaining activity at the higher temperatures. Any of the known techniques for protein mutagenesis may be employed, with particularly preferred mutagenesis techniques being those discussed above.

As a representative list of enzymes which may be mutagenized in accordance with the aspects of the present invention, there may be mentioned, the following enzymes and their functions:

1 Lipase/Esterase
   a. Enantioselective hydrolysis of esters (lipids)/thioesters
      1) Resolution of racemic mixtures
      2) Synthesis of optically active acids or alcohols from meso-diesters
   b. Selective syntheses
      1) Regiospecific hydrolysis of carbohydrate esters
      2) Selective hydrolysis of cyclic secondary alcohols
   c. Synthesis of optically active esters, lactones, acids, alcohols
      1) Transesterification of activated/nonactivated esters
      2) Interesterification
      3) Optically active lactones from hydroxyesters
      4) Regio- and enantioselective ring opening of anhydrides
   d. Detergents
   e. Fat/Oil conversion
   f. Cheese ripening 2 Protease
   a. Ester/amide synthesis
   b. Peptide synthesis
   c. Resolution of racemic mixtures of amino acid esters
   d. Synthesis of non-natural amino acids
   e. Detergents/protein hydrolysis 3 Glycosidase/Glycosyl transferase
   a. Sugar/polymer synthesis
   b. Cleavage of glycosidic linkages to form mono, di- and oligosaccharides
   c. Synthesis of complex oligosaccharides d. Glycoside synthesis using UDP-galactosyl transferase
e. Transglycosylation of disaccharides, glycosyl fluorides, aryl galactosides
f. Glycosyl transfer in oligosaccharide synthesis
g. Diastereoselective cleavage of β-glucosylsulfoxides
h. Asymmetric glycosylations
i. Food processing
j. Paper processing 4 Phosphatase/Kinase
   a. Synthesis/hydrolysis of phosphate esters
      1) Regio-, enantioselective phosphorylation
      2) Introduction of phosphate esters
      3) Synthesize phospholipid precursors
      4) Controlled polynucleotide synthesis
   b. Activate biological molecule
   c. Selective phosphate bond formation without protecting groups 5 Mono/Dioxygenase
   a. Direct oxyfunctionalization of unactivated organic substrates
   b. Hydroxylation of alkane, aromatics, steroids
   c. Epoxidation of alkenes
   d. Enantioselective sulphoxidation
   e. Regio- and stereoselective Bayer-Villiger oxidations 6 Haloperoxidase
   a. Oxidative addition of halide ion to nucleophilic sites
   b. Addition of hypohalous acids to olefinic bonds
   c. Ring cleavage of cyclopropanes
   d. Activated aromatic substrates converted to ortho and para derivatives
   e. 1.3 diketones converted to 2-halo-derivatives
   f. Heteroatom oxidation of sulfur and nitrogen containing substrates
   g. Oxidation of enol acetates, alkynes and activated aromatic rings 7 Lignin peroxidase/Diarylpropane peroxidase
   a. Oxidative cleavage of C—C bonds
   b. Oxidation of benzylic alcohols to aldehydes
   c. Hydroxylation of benzylic carbons
   d. Phenol dimerization
   e. Hydroxylation of double bonds to form diols
   f. Cleavage of lignin aldehydes 8 Epoxide hydrolase
   a. Synthesis of enantiomerically pure bioactive compounds
   b. Regio- and enantioselective hydrolysis of epoxide
   c. Aromatic and olefinic epoxidation by monooxygenases to form epoxides
   d. Resolution of racemic epoxides
   e. Hydrolysis of steroid epoxides 9 Nitrile hydratase/nitrilase
   a. Hydrolysis of aliphatic nitrites to carboxamides
   b. Hydrolysis of aromatic, heterocyclic, unsaturated aliphatic nitrites to corresponding acids
   c. Hydrolysis of acrylonitrile
   d. Production of aromatic and carboxamides, carboxylic acids (nicotinamide, picolinamide, isonicotinamide)
   e. Regioselective hydrolysis of acrylic dinitrile
   f. α-amino acids from α-hydroxynitriles 10 Transaminase
   a. Transfer of amino groups into oxo-acids 11 Amidase/Acylase
   a. Hydrolysis of amides, amidines, and other C—N bonds
   b. Non-natural amino acid resolution and synthesis The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

EXAMPLE 1

Mutagenesis of Positive Enzyme Activity Clones

Mutagenesis was performed on two different enzymes (alkaline phosphatase and β-glycosidase), using the two different strategies described here, to generate new enzymes which exhibit a higher degree of activity at lower temperatures than the wild-type enzymes.

Alkaline Phosphatase

The XL1-Red strain (Stratagene) was transformed with DNA encoding an alkaline phosphatase (in plasmid pBluescript) from the organism OC9a according to the manufacturer's protocol. A 5 ml culture of LB+0.1 mg/ml ampicillin was inoculated with 200 μl of the transformation. The culture was allowed to grow at 37° C. for 30 hours. A miniprep was then performed on the culture, and screening was performed by transforming 2 μl of the resulting DNA into XL-1 Blue cells (Stratagene) according to the manufacturer's protocol.

Standard Alkaline Phosphatase Screening Assay
→Plate on LB/amp plates→Lift colonies with Duralon UV (Stratagene) or HATF (Millipore) membranes→Lyse in chloroform vapors for 30 seconds→Heat kill for 30 minutes at 85° C.→Develop filter at room temperature in BCIP buffer→Watch as filter develops and identify and pick fastest developing colonies ("positives")→Restreak "positives" onto a BCIP plate.

BCIP Buffer:
   20 mm CAPS pH 9.0
   1 mm $MgCl_2$
   0.01 mm $ZnCl_2$
   0.1 mg/ml BCIP The mutated OC9a phosphatase took 10 minutes to develop color and the wild type enzyme took 30 minutes to develop color in the screening assay.

Beta-Glycosidase

This protocol was used to mutagenize DNA encoding Thermococcus 9N2 Beta-Glycosidase. This DNA sequence is set forth in FIG. 1.

PCR
   2 microliters dNTP's (10 mM Stocks)
   10 microliters 10 xPCR Buffer
   0.5 microliters pBluescript vector containing Beta-glycosidase DNA (100 nanograms)
   20 microliters 3' Primer (100 pmol)
   20 microliters 5' Primer (100 pmol)
   16 microliters $MnCl\ 4H_2O$ (1.25 mM Stock)
   24.5 microliters $H_2O$
   1 microliter Taq Polymerase (5.0 Units)
   100 microliters total Reaction Cycle
95° C. 15 seconds
58° C. 30 seconds
72° C. 90 seconds
25 cycles (10 minute extension at 72° C.–4° C. incubation)
Run 5 microliters on a 1% agarose gel to check the reaction.
Purify on a Qiaquick column (Qiagen).
Resuspend in 50 microliters H₂O.
Restriction Digest
25 microliters purified PCR product
10 microliters NEB Buffer #2
3 microliters Kpn I (10U/microliter)
3 microliters EcoR1 (20U/microliter)
59 microliters H₂O
Cut for 2 hours at 37° C.
Purify on a Qiaquick column (Qiagen).
Elute with 35 microliters H₂O.
Ligation
10 microliters Digested PCR product
5 microliters pBluescript Vector (cut with EcoRI/KpnI and phosphatased with shrimp alkaline phosphatase)
4 microliters 5× Ligation Buffer
1 microliter T4 DNA Ligase (BRL)
Ligate overnight.
Transform into M15pREP4 cells using electroporation.
Plate 100 or 200 microliters onto LB amp meth kan plates, grow overnight at 37 degrees celsius.
Beta-Glycosidase Assay
Perform glycosidase assay to screen for mutants as follows. The filter assay uses buffer Z (see recipe below) containing 1 mg/ml of the substrate 5-bromo-4-chloro-3-indolyl-β-o-glucopyranoside (XGLU) (Diagnostic Chemicals Limited or Sigma).

Z-Buffer: (referenced in Miller, J. H. (1992) A Short Course in Bacterial Genetics, p. 445.)
per liter:

| | |
|---|---|
| Na₂HPO₄-7H₂O | 16.1 g |
| NaH₂PO₄—H₂O | 5.5 g |
| KCl | 0.75 g |
| MgSO₄-7H₂O | 0.246 g |
| β-mercaptoethanol | 2.7 ml |
| Adjust pH to 7.0 | |

(1) Perform colony lifts using Millipore HATF membrane filters.
(2) Lyse colonies with chloroform vapor in 150 mm glass petri dishes.
(3) Transfer filters to 100 mm glass petri dishes containing a piece of Whatman 3MM filter paper saturated with Z buffer containing 1 mg/ml XGLU. After transferring filter bearing lysed colonies to the glass petri dish, maintain dish at room temperature.
(4) "Positives" were observed as blue spots on the filter membranes ("positives" are spots which appear early). Use the following filter rescue technique to retrieve plasmid from lysed positive colony. Use pasteur pipette (or glass capillary tube) to core blue spots on the filter membrane. Place the small filter disk in an Epp tube containing 20 μl water. Incubate the Epp tube at 75° C. for 5 minutes followed by vortexing to elute plasmid DNA off filter. Transform this DNA into electrocompetent E. coli cells. Repeat filter-lift assay on transformation plates to identify "positives." Return transformation plates to 37° C. incubator after filter lift to regenerate colonies. Inoculate 3 ml LBamp liquid with repurified positives and incubate at 37° C. overnight. Isolate plasmid DNA from these cultures and sequence plasmid insert.

The β-glycosidase subjected to mutagenesis acted on XGLU 2.5 times more efficiently than wild-type β-glycosidase.

What is claimed is:

1. A method of producing a thermostable enzyme which is stable at temperatures of at least 60° C. and which exhibits higher activity at a desired lower temperature below 60° C., compared with a corresponding wild-type enzyme at its optimal temperature, comprising:
   (a) isolating nucleic acid from a thermophilic organism, said nucleic acid comprising at least one polynucleotide encoding a desired enzyme which is stable at a temperature of at least 60° C.;
   (b) preparing a library of clones generated from the nucleic acid of step (a);
   (c) mutating the nucleic acid sequence contained in a clone from the library comprising the at least one polynucleotide of step (a); and
   (d) screening mutants produced by the mutating step (c) to identify a mutated enzyme or a polynucleotide encoding a mutated enzyme, wherein the mutated enzyme is stable at a temperature of at least 60° C., and has increased enzyme activity at a lower temperature than the activity of the corresponding wild-type enzyme at its optimal temperature.

2. The method according to claim 1, wherein the thermophilic organism is selected from eubacteria or archaebacteria.

3. The method according to claim 1, wherein the thermophilic organism is obtained from an environment selected from hot springs, tropical areas, or volcanic areas.

4. The method according to claim 1, wherein the isolated nucleic acid comprising the at least one polynucleotide is inserted into a vector selected from the group consisting of viral vectors, baculovirus vectors, phage vectors, plasmid vectors, phagemid vectors, cosmid vectors, phosmid vectors, bacterial artificial chromosome (BAC) vectors, P1-based artificial chromosome vectors, yeast plasmid vectors, yeast artificial chromosome (YAC) vectors and fungal vectors.

5. The method according to claim 4, wherein the vector comprises one or more selectable marker genes.

6. The method according to claim 1, wherein the library is an expression library and the nucleic acid is contained in expression vectors.

7. The method according to claim 6, wherein the expression vectors are introduced into a host cell for expression.

8. The method according to claim 7, wherein the host cells are eukaryotic, prokaryotic, or mammalian host cells.

9. The method according to claim 1, wherein the enzyme is stable at a temperature of at least 70° C.

10. The method according to claim 1, wherein the activity of the mutated enzyme is at least two-fold greater than the activity of the corresponding wild-type enzyme.

11. The method according to claim 1, wherein the activity of the mutated enzyme is at least four-fold greater than the activity of the corresponding wild-type enzyme.

12. The method according to claim 1, wherein the activity of the mutated enzyme is at least ten-fold greater than the activity of the corresponding wild-type enzyme.

13. The method according claim 1, wherein the enzyme activity of the mutated enzyme is increased at a temperature below at least 55° C.

14. The method according to claim 1, wherein the enzyme activity of the mutated enzyme is increased at a temperature below at least 50° C.

15. The method according to claim 1, wherein the enzyme activity of the mutated enzyme is increased at a temperature below at least 40° C.

16. The method according to claim 1, wherein the enzyme activity of the mutated enzyme is increased at a temperature below at least 30° C.

17. The method according to claim 1, wherein the mutating step (c) comprises error-prone PCR.

18. The method according to claim 1, wherein the mutating step (c) comprises oligonucleotide-directed mutagenesis.

19. The method according to claim 1, wherein the mutating step (c) comprises sexual PCR mutagenesis.

20. The method according to claim 1, wherein the mutating step (c) comprises cassette mutagenesis.

21. The method according to claim 1, wherein the mutating step (c) comprises recursive ensemble mutagenesis.

22. The method according to claim 1, wherein the mutating step (c) comprises exponential ensemble mutagenesis.

23. The method according to claim 22, wherein the exponential ensemble mutagenesis is performed in vitro.

24. The method according to claim 1, wherein the mutated enzyme is a phosphatase.

25. The method according to claim 1, wherein the mutated enzyme is a lipase.

26. The method according to claim 1, wherein the mutated enzyme is an esterase.

27. The method according to claim 1, wherein the mutated enzyme is a protease.

28. The method according to claim 1, wherein the mutated enzyme is a glycosidase or glycosyl transferase.

29. The method according to claim 1, wherein the mutated enzyme is a kinase.

30. The method according to claim 1, wherein the mutated enzyme is a mono-oxygenase or a di-oxygenase.

31. The method according to claim 1, wherein the mutated enzyme is a peroxidase or haloperoxidase.

32. The method according to claim 1, wherein the mutated enzyme is a hydrolase or epoxide hydrolase.

33. The method according to claim 1, wherein the mutated enzyme is a nitrile hydratase or nitrilase.

34. The method according to claim 1, wherein the mutated enzyme is a transaminase.

35. The method according to claim 1, wherein the mutated enzyme is an amidase or acylase.

36. A method of producing a thermostable enzyme, said enzyme being stable at a temperature of at least 60° C. and having activity at a temperature of less than 60° C. that is higher than the corresponding activity of a wild-type enzyme, comprising:
(a) inserting nucleic acid isolated from a thermostable organism into an expression vector, said nucleic acid encoding at least one enzyme which is stable at a temperature of at least 60° C.;
(b) preparing an expression library containing the isolated nucleic acid of step (a) in a suitable host cell;
(c) subjecting the library to random mutagenesis; and
(d) screening mutants produced in (c) for a mutated enzyme or for a polynucleotide encoding a mutated enzyme, wherein the mutated enzyme is stable at a temperature of at least 60° C. and has increased enzyme activity at a lower temperature than the activity of a corresponding wild-type enzyme at its optimal temperature.

37. The method according to claim 36, wherein the thermostable organism is selected from eubacteria or archaebacteria.

38. The method according to claim 36, wherein the thermostable organism is obtained an from hot springs, volcanic areas, or tropical areas.

39. The method according to claim 36, wherein the expression library comprises a vector selected from the group consisting of viral vectors, baculovirus vectors, phage vectors, plasmid vectors, phagemid vectors, cosmid vectors, phosmid vectors, bacterial artificial chromosome (BAC) vectors, P1-based artificial chromosome vectors, yeast plasmid vectors, yeast artificial chromosome (YAC) vectors and fungal vectors.

40. The method according to claim 39, wherein the vector comprises one or more selectable marker genes.

41. The method according to claim 36, wherein the enzyme is stable at a temperature of at least 70° C.

42. The method according to claim 36, wherein the activity of the mutated enzyme is at least two-fold greater than the activity of the corresponding wild-type enzyme.

43. The method according to claim 36, wherein the activity of the mutated enzyme is at least four-fold greater than the activity of the corresponding wild-type enzyme.

44. The method according to claim 36, wherein the activity of the mutated enzyme is at least ten-fold greater than the activity of the corresponding wild-type enzyme.

45. The method according to claim 36, wherein the enzyme activity of the mutated enzyme is increased at a temperature below at least 55° C.

46. The method according to claim 36, wherein the enzyme activity of the mutated enzyme is increased at a temperature below at least 50° C.

47. The method according to claim 36, wherein the enzyme activity of the mutated enzyme is increased at a temperature below at least 40° C.

48. The method according to claim 36, wherein the enzyme activity of the mutated enzyme is increased at a temperature below at least 30° C.

49. The method according to claim 36, wherein the mutagenesis of step (c) comprises error-prone PCR.

50. The method according to claim 36, wherein the mutagenesis of step (c) comprises oligonucleotide-directed mutagenesis.

51. The method according to claim 36, wherein the mutagenesis of step (c) comprises sexual PCR mutagenesis.

52. The method according to claim 36, wherein the mutagenesis of step (c) comprises cassette mutagenesis.

53. The method according to claim 36, wherein the mutagenesis of step (c) comprises recursive ensemble mutagenesis.

54. The method according to claim 36, wherein the mutagenesis of step (c) comprises exponential ensemble mutagenesis.

55. The method according to claim 36, wherein the exponential ensemble mutagenesis is performed in vitro.

56. The method according to claim 36, wherein the mutated enzyme is a phosphatase.

57. The method according to claim 36, wherein the mutated enzyme is a lipase.

58. The method according to claim 36, wherein the mutated enzyme is an esterase.

59. The method according to claim 36, wherein the mutated enzyme is a protease.

60. The method according to claim 36, wherein the mutated enzyme is a glycosidase or glycosyl transferase.

61. The method according to claim 36, wherein the mutated enzyme is a kinase.

62. The method according to claim 36, wherein the mutated enzyme is a mono-oxygenase or a di-oxygenase.

63. The method according to claim 36, wherein the mutated enzyme is a peroxidase or haloperoxidase.

64. The method according to clam 36, wherein the mutated enzyme is a hydrolase or epoxide hydrolase.

65. The method according to claim 36, wherein the mutated enzyme is a nitrile hydratase or nitrilase.

66. The method according to claim 36, wherein the mutated enzyme is a transaminase.

67. The method according to claim 36, wherein the mutated enzyme is an amidase or acylase.

68. A method of producing an enzyme that is stable at temperatures of at least 60° C., said enzyme having higher enzyme activity at a temperature lower than 60° C., compared with the activity of a corresponding wild-type enzyme at its optimal temperature, comprising:
(a) isolating from a thermophilic organism at least one polynucleotide encoding a desired enzyme which is stable at a temperature of at least 60° C.;
introducing the at least one polynucleotide of step (a) into a host organism having at least one deletion in its nucleic acid repair genes so as to mutate the at least one introduced polynucleotide encoding the desired enzyme so as to produce a mutated enzyme; and
(c) screening nucleic acid or expression products from the host organism for a mutated enzyme, or for at least one polynucleotide encoding a mutated enzyme, said enzyme being stable at a temperature of at least 60° C. and having increased enzyme activity at a lower temperature than the activity of a corresponding wild-type enzyme at its optimal temperature.

69. The method according to claim 68, wherein the thermophilic organism is eubacteria or archaebacteria.

70. The method according to claim 68, wherein the thermophilic organism is obtained from an environment selected from hot springs, volcanic areas, or tropical areas.

71. The method according to claim 68, wherein the host organism of step (b) is a mutant strain of *E. coil.*

72. The method according to claim 68, wherein the enzyme is stable at a temperature of at least 70° C.

73. The method according to claim 68, wherein the activity of the mutated enzyme is at least two-fold greater than the activity of the corresponding wild-type enzyme.

74. The method according to claim 68, wherein the activity of the mutated enzyme is at least four-fold greater than the activity of the corresponding wild-type enzyme.

75. The method according to claim 68, wherein the activity of the mutated enzyme is at least ten-fold greater than the activity of the corresponding wild-type enzyme.

76. The method according to claim 68, wherein the enzyme activity of the mutated enzyme is increased at a temperature below at least 55° C.

77. The method according to claim 68, wherein the enzyme activity of the mutated enzyme is increased at a temperature below at least 50° C.

78. The method according to claim 68, wherein the enzyme activity of the mutated enzyme is increased at a temperature below at least 40° C.

79. The method according to claim 68, wherein the enzyme activity of the mutated enzyme is increased at a temperature below at least 30° C.

80. The method according to claim 68, wherein the mutated enzyme is produced by in vivo mutagenesis.

81. The method according to claim 68, wherein the mutated enzyme is a phosphatase.

82. The method according to claim 68, wherein the mutated enzyme is a lipase.

83. The method according to claim 68, wherein the mutated enzyme is at esterase.

84. The method according to claim 68, wherein the mutated enzyme is a protease.

85. The method according to claim 68, wherein the mutated enzyme is a glycosidase or glycosyl transferase.

86. The method according to claim 68, wherein the mutated enzyme is a kinase.

87. The method according to claim 68, wherein the mutated enzyme is a mono-oxygenase or a di-oxygenase.

88. The method according to claim 68, wherein the mutated enzyme is a peroxidase or haloperoxidase.

89. The method according to claim 68, wherein the mutated enzyme is a hydrolase or epoxide hydrolase.

90. The method according to claim 68, wherein the mutated enzyme is a nitrile hydratase or nitrilase.

91. The method according to claim 68, wherein the mutated enzyme is a transaminase.

92. The method according to claim 68, wherein the mutated enzyme is an amidase or acylase.

* * * * *